US008633703B2

(12) United States Patent
Eberheim et al.

(10) Patent No.: US 8,633,703 B2
(45) Date of Patent: Jan. 21, 2014

(54) INDUCTIVE CONDUCTIVITY SENSOR

(75) Inventors: Andreas Eberheim, Waldheim (DE); Torsten Pechstein, Radebeul (DE); Marco Volker, Karlsruhe (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 360 days.

(21) Appl. No.: 13/058,882

(22) PCT Filed: Aug. 3, 2009

(86) PCT No.: PCT/EP2009/060033
§ 371 (c)(1),
(2), (4) Date: Feb. 14, 2011

(87) PCT Pub. No.: WO2010/018098
PCT Pub. Date: Feb. 18, 2010

(65) Prior Publication Data
US 2011/0140718 A1    Jun. 16, 2011

(30) Foreign Application Priority Data
Aug. 15, 2008  (DE) .................. 10 2008 037 893

(51) Int. Cl.
*G01N 27/02*    (2006.01)
(52) U.S. Cl.
USPC .................. 324/445; 324/691; 324/654
(58) Field of Classification Search
USPC ........................................... 324/445
See application file for complete search history.

(56) References Cited

U.S. PATENT DOCUMENTS

| 2,542,057 | A | 2/1951 | Relis |
| 3,054,946 | A | 9/1962 | Esterson |
| 5,793,214 | A | 8/1998 | Wakamatsu |
| 7,906,371 | B2 * | 3/2011 | Kim et al. ...................... 438/113 |
| 7,965,167 | B2 * | 6/2011 | Volker et al. .................. 336/229 |
| 2007/0008060 | A1 | 1/2007 | Weller |

FOREIGN PATENT DOCUMENTS

| DE | 690 22 397 T2 | 3/1996 |
| DE | 10 2006 025 194 | * 10/2006 |
| DE | 10 2006 025 194 A1 | 12/2007 |
| EP | 0 883 328 A1 | 12/1998 |

* cited by examiner

*Primary Examiner* — Arleen M Vazquez
*Assistant Examiner* — Feba Pothen
(74) *Attorney, Agent, or Firm* — Bacon & Thomas, PLLC

(57) ABSTRACT

A conductivity sensor for measuring conductivity of a medium surrounding the conductivity sensor, including: a first toroidal coil, which surrounds a first traversing opening for accommodating the medium and which serves for inducing an electrical current in the medium, a second toroidal coil, which surrounds a second traversing opening for accommodating the medium and which serves for registering a magnetic field produced by the induced electrical current. At least one of the toroidal coils has a plurality of first conductor sections, which extend in a plane of a multi-ply circuit card, a plurality of second conductor sections, which extend in a second plane of the circuit card, and a plurality of first vias, which connect the first conductor sections with the second conductor sections. The first conductor sections, the second conductor sections and the vias together form the windings of a toroidal coil, wherein at least one toroidal coil is surrounded by a plurality of internally metallized bores, which are arranged in such a manner, that they act as electrical shielding of the toroidal coil.

9 Claims, 2 Drawing Sheets

INDUCTIVE CONDUCTIVITY SENSOR

TECHNICAL FIELD

The invention relates to an inductive conductivity sensor for measuring electrical conductivity of a medium surrounding the conductivity sensor.

BACKGROUND DISCUSSION

Such conductivity sensors comprise essentially a transmitting coil and a receiving coil, which, as a rule, are embodied as toroidal coils, and which surround a traversing opening for accommodating the medium, so that, in the case of exciting the transmitting coil, a closed circuit path can form extending within the medium and passing through the transmitting and receiving coils. An inductive conductivity sensor can be described as a combination of two transformers, wherein the closed path acts as a coil with a winding belonging to both transformers. Through evaluation of the signal of the receiving coil in response to the signal of the transmitting coil, consequently, the conductivity of the medium can be ascertained.

From the state of the art, for example, from DE 10 2007 039015 A1, known inductive conductivity sensors are usually shielded against capacitive and inductive coupling with the aid of conductive supports, or housings, and shieldings of high permeability material.

From DE 10 2006 025 194 A1, a conductivity sensor is known, whose toroidal coils are formed of a plurality of first conductor sections, which extend in a plane of a multi-ply circuit card, a plurality of second conductor sections, which extend in a second plane of the circuit card, and a plurality of vias, which connect the first conductor sections with the second conductor sections, in order to form coil windings. In a form of embodiment, the coils are arranged coaxially and axially one after the other within the circuit card. Extending between the two coils within the circuit is an additional separating ply card, which can serve as a shielding ply for decoupling the coils.

Such a separating ply enables, however, only a shielding parallel to the base surfaces of the toroidal coils, however, not along its periphery. Correspondingly, toroidal coils with parallel central axes arranged next to one another, or coaxial coplanarly arranged toroidal coils, can then not be shielded sufficiently relative to one another. An encapsulation of the individual toroidal coils integrated in a circuit card, in each case, in their own housings, which shield the two coils relative to one another, introduces a number of disadvantages. Especially, in this way, a number of advantages of the integration of the conductivity sensor in a circuit card must be abandoned, such as, for example, simplified, automated manufacture or the compactness of the sensor construction.

SUMMARY OF THE INVENTION

Thus, an object of the present invention is to overcome the disadvantages of the state of the art, and, especially, to provide an effective shielding for a conductivity sensor integrated in a circuit card, especially a shielding suitable for coplanar coil arrangements.

This object is achieved by a conductivity sensor for measuring conductivity of a medium surrounding the conductivity sensor, comprising: A first toroidal coil, which surrounds a first traversing opening for accommodating the medium and which serves for inducing an electrical current in the medium, a second toroidal coil, which surrounds a second traversing opening for accommodating the medium and which serves for registering a magnetic field produced by the induced electrical current, wherein at least one of the toroidal coils, especially each toroidal coil, has a plurality of first conductor sections, which extend in a first plane of a multi-ply circuit card, and a plurality of second conductor sections, which extend in a second plane of the circuit card, and a plurality of vias, which connect the first conductor sections with the second conductor sections, wherein the first conductor sections, the second conductor sections and the vias together form the windings of the toroidal coil, and wherein the at least one toroidal coil, especially each toroidal coil, is surrounded by a plurality of internally metallized bores, which are located within the circuit card and which are arranged in such a manner that they act as electrical shielding of the toroidal coil.

The term "toroidal coil" means a coil with a closed magnetic path extending within the coil windings. When thus a magnet core is provided, such must be in the form of a closed loop or at least a loop interrupted only by air gaps. The same is true for a hollow space filled with gas or a non-magnetic material, e.g. the circuit card material, in the case of a coreless toroidal coil. The shape of the closed loop is not decisive. A circular ring is the simplest shape, equally, however, also any other forms are options, such as, for example, ellipses, rectangles or other polygons. The toroidal coils have a central axis, which, in the case of a circular ring coil, is a rotational symmetry axis. In case the toroidal coil has no cylindrical symmetry, but, instead, for example, is embodied as an ellipse or a polygon, the central axis extends, for example, through the midpoint of the polygon, or through a central point within the ellipse located between the elliptical focal points.

A multi-ply circuit card has a number of planes or plies stacked layer-wise in a stack direction one after the other, and conductive traces or conductor sections or other components can be arranged in these planes or plies.

The first traversing opening surrounded by the first toroidal coil and the second traversing opening surrounded by the second toroidal coil can be separated spatially from one another or they can coincide. Thus, the first and second openings in the case of coaxial coils lying axially one after the other are arranged directly against one another and one after the other. In the case of a coaxial coplanar arrangement of the toroidal coils, the first and second openings are a single central traversing opening surrounded by both coils.

The internally metallized bores can be embodied, for example, as vias of the circuit card, in the case of which the inner walls are provided with a metal layer. Established methods exist for the manufacture of such vies. With the internally metallized bores, consequently, an effective, yet simply manufactured shielding can be provided for the toroidal coils.

Preferably, the bores extend essentially parallel to the vias of the toroidal coils. Especially, the bores can extend, as the vias, essentially perpendicular to the plies of the circuit card, thus extending perpendicularly, in the stack direction.

In an embodiment, the plurality of internally metallized bores includes a first group of internally metallized bores, in the following referred to as "bores of first type", which are arranged along an essentially closed ring surrounded by the at least one toroidal coil around the traversing opening of the toroidal coil. The term "ring" refers also here to an essentially closed path, whose exact shape is not decisive, and which can be embodied e.g. circularly, elliptically, polygonally or in irregular manner. In such case, these bores extend ideally essentially parallel to the vies of the toroidal coil windings, and, respectively, essentially perpendicularly to the plies of the circuit card.

The bores of first type are arranged, thus, between an inner periphery of the toroidal coil and the traversing opening surrounded by the toroidal coil and accommodating medium. The inner periphery of the toroidal coil is formed by the inner vias of the toroidal coil inwardly forming the toroidal coil and extending parallel to the bores. For example, in the case of a rotationally symmetric toroidal coil, its inner periphery corresponds to a cylindrical lateral surface, which is surrounded by the inner vias of the toroidal coil. The bores of first type extend, in this case, preferably essentially parallel to the rotational symmetry axis of the toroidal coil and are arranged all around the cylindrical lateral surface.

In an additional embodiment, the plurality of internally metallized bores includes a second group of internally metallized bores, in the following referred to as "bores of second type", which are arranged along an essentially closed ring around the at least one toroidal coil. Also here, the term "ring" means an essentially closed path, which, for example, can be embodied circularly, elliptically, polygonally or in irregular manner. In such case, these bores extend ideally essentially parallel to the vies of the toroidal coil windings, or essentially perpendicularly to the plies of the circuit card.

The bores of second type thus surround an outer periphery of the toroidal coil, which is formed by the outer vies of the toroidal coil windings forming the outer boundary of the toroidal coil. In the case of a rotationally symmetric toroidal coil, the outer periphery of the toroidal coil corresponds, for example, to a cylindrical lateral surface extending perpendicular to the circuit card planes and encasing the toroidal coil. The bores of second type extend, in this special case, parallel to the cylindrical symmetry axis of the toroidal coil and are arranged all around the cylindrical lateral surface enveloping the toroidal coil.

The terms "internally" or "inwardly" mean a direction essentially parallel to the circuit card plies and toward the central axis of the toroidal coil. The terms "externally" or "outwardly" mean, correspondingly, the opposite direction.

In an additional embodiment, in at least one further, third plane of the circuit card, there is arranged a shielding ply for electrical shielding, in the following also referred to as "electrical shielding ply", especially a ply of an electrically conductive metal, such as e.g. copper, wherein at least one of the toroidal coils is arranged, in the stack direction of the circuit card, before or behind the electrical shielding ply. In this case, especially the first and the second planes, in which the first and second conductor sections of the toroidal coil are arranged, are arranged in the stack direction of the circuit card before or behind the shielding ply.

In a preferred further development of this embodiment, there are arranged, in the third plane of the circuit card, a first electrical shielding ply, and in an additional fourth plane of the circuit card, a second electrical shielding ply, wherein the at least one toroidal coil, referenced to the stack direction of the circuit card, is arranged between the first and the second shielding ply, wherein especially the first and the second planes, in which the first and second conductor sections of the toroidal coil are arranged, are arranged between the first and the second shielding plies.

These electrical shielding plies serve for shielding the toroidal coils on their base surfaces. Together with the metallized bores extending essentially perpendicularly to the shielding plies, there is formed a kind of encapsulation of the toroidal coils.

Especially suitable for producing an encompassing shielding is an embodiment, in the case of which the bores of first type are, in each case, directly connected with only one of the shielding plies, and wherein the bores of second type connect the first and second electrical shielding plies with one another. In this way, an electrical shielding of the toroidal coil in all spatial directions is assured. Since the bores of first type, however, are connected with only one of the shielding plies directly, there arises a surrounding gap in the shielding of the toroidal coil, by which the forming of eddy currents within the shielding is prevented.

In a, to this, alternative embodiment, the bores of first type connect the first and second shielding plies with one another, while the bores of second type are directly connected, in each case, with only one of the electrical shielding plies. This alternative embodiment has yet the additional advantage, that the surrounding gap in the shielding is arranged in the outer region of the toroidal coil, so that occurring stray fields present there have an as large as possible separation from one another.

In this case, it is especially advantageous, when the bores of second type comprise a first group of bores, which are directly connected with the first electrical shielding ply, and a second group of bores, which are conductively connected with the second electrical shielding ply, wherein the first and second electrical shielding plies are arranged, in each case, on opposing sides of the at least one toroidal coil. In such case, the bores of the first and second groups extend in the stack direction of the circuit card preferably through the same circuit card plies as the vias of the toroidal coil. In this way, there results an overlap of the shielding provided by the bores of the first group with the shielding provided by the bores of the second group. This type of shielding is only slightly less effective than a shielding with contactings traversing between the first and second shielding plies.

In an additional embodiment, at least one of the toroidal coils includes a toroidal core, especially composed of at least one annular foil or a solid or layered core material. The core material can be implemented, for example, in the form of a solid magnetic material, a wound or layered magnetic foil or a solid insulating matrix, e.g. of synthetic material. e.g. plastic, or ceramic with magnetic particles or a wound or layered insulating foil matrix, e.g. of synthetic material, e.g. plastic, or a ceramic, with magnetic particles. The toroidal core can be mounted in a cavity, e.g. by lamination or deposition or gluing, in the manufacture of the circuit card.

In an additional embodiment, the first and second toroidal coils are arranged coplanarly and coaxially, wherein the first and second toroidal coils have a shared central axis, especially a rotational symmetry axis.

In an alternative embodiment, the first and second toroidal coils are arranged coplanarly and axially parallel next to one another, wherein the first and second toroidal coils have central axes spaced from one another, especially rotational symmetry axes.

In an alternative embodiment, the first and second toroidal coils are arranged coaxially and axially sequenced one after the other and have a shared central axis, especially a rotational symmetry axis, wherein at least one shielding ply is arranged in the circuit card between the toroidal coils for magnetic shielding. In this embodiment, the arrangement of a magnetic shielding ply between the toroidal coils is advantageous for lessening inductive coupling. In the case of the described embodiments in the two preceding paragraphs, in the case of which the toroidal coils are arranged coplanarly, the inductive coupling is markedly smaller, so that such an additional magnetic shielding ply can, in given cases, be omitted.

Advantageously, the at least one shielding ply for magnetic shielding comprises a high permeability material, which at least has a relative permeability of more than 1000.

BRIEF DESCRIPTION OF THE DRAWINGS

The invention will now be explained based on the example of an embodiment illustrated in the drawing, the figures of which show as follows.

DETAILED DISCUSSION IN CONJUNCTION WITH THE DRAWINGS

Figure 1:
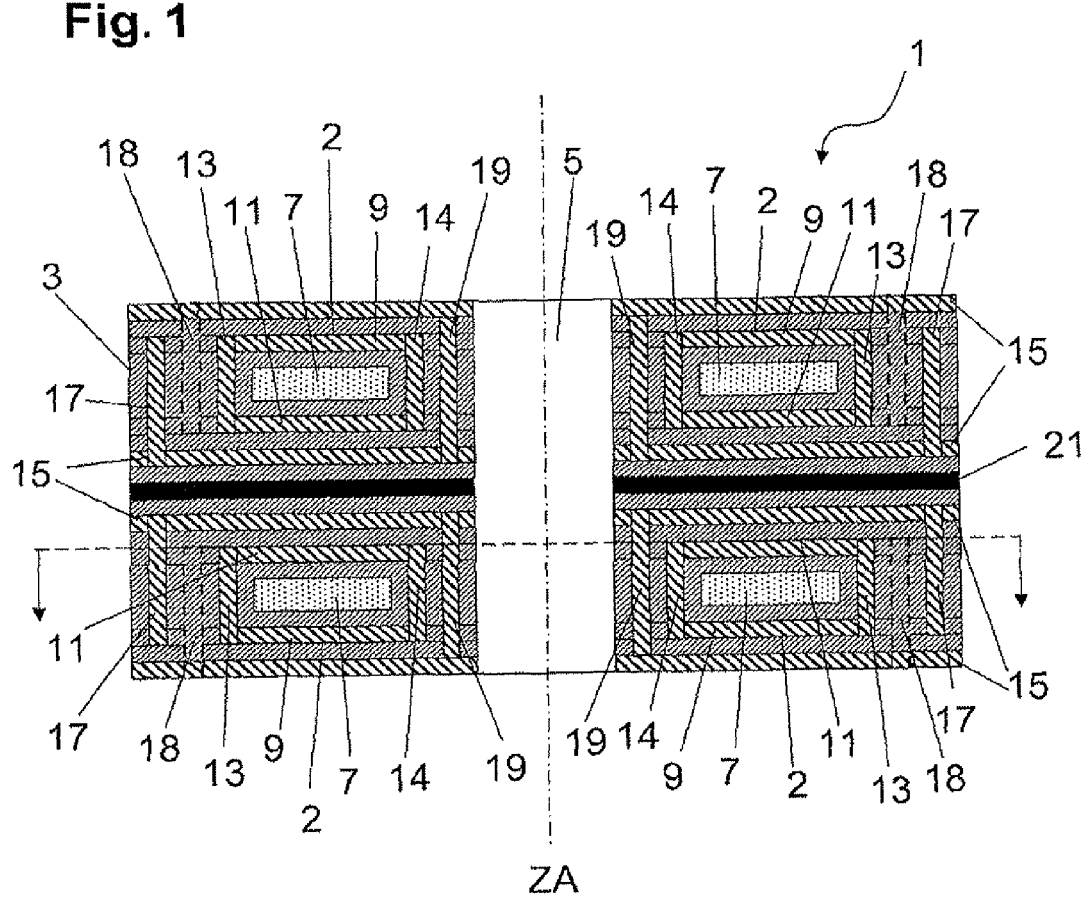
FIG. 1 is a sectional illustration of a circuit card integrated, conductivity sensor having a shielding according to an embodiment of the invention.

FIG. 1 shows a longitudinal section through a coil arrangement 1 in a conductivity sensor in a multi-ply circuit card 3. The coil arrangement 1 includes two toroidal coils 2, which annularly surround a traversing opening 5 in the circuit card 3. The coil windings of the toroidal coils 2 are formed by first conductor sections 9, second conductor sections 11, inner vias 14 and outer vias 13. The inner vias 14 serve to provide electrically conductive connections between the inner ends of the conductor sections 9 and 11 adjoining the central axis ZA of the toroidal coils 2, while the outer vias 13 provide conductive connections between the outer ends of the conductor sections 9 and 11 remote from the central axis ZA. In the example of FIG. 1, the central axis ZA is a rotational symmetry axis of the cylindrically symmetrical, toroidal coils 2.

Between the different planes of the circuit card, in which the conductor sections 9 and 11 extend, an intermediate ply is arranged, which can comprise one or a number of plies of the circuit card 3. The intermediate ply has a cavity, in which, in each case, a toroidal core 7 is provided for the toroidal coils 2. The conductor sections 9 and 11 and the vias 13 and 14 surround the toroidal core 7.

The two toroidal coils 2 of the coil arrangement 1 are arranged in the present example coaxially and axially one after the other with reference to a shared rotational symmetry axis ZA, so that the traversing openings surrounded by each individual toroidal coil 2 adjoin one another and form a single traversing opening 5 extending along the rotational symmetry axis ZA. Extending between the axially adjoining, toroidal coils 2 is a separating ply 21, which can comprise one or a number of ply portions, for example, shielding plies, especially for the inductive decoupling of the toroidal coils.

Arranged in the stack direction of the circuit card 3 before and behind the toroidal coils 2 are electrical shielding plies of an electrically conductive material, such as e.g. copper, which are electrically insulated from the conductor sections 9 and 11, as well as from the vias 13 and 14. Each of the toroidal coils 2 is thus arranged with reference to the stack direction of the circuit card 3 between two shielding plies 15.

For protection against aggressive measured media, the circuit card 3, especially the shielding plies 15 in the wettable region, can be coated with a plastic or other synthetic material, protective layer (not shown).

Arranged along the inner periphery of the toroidal coils 2 formed by the inner vias 14 are a plurality of internally metallized bores 19 extending parallel to the vias 13, 14 along an essentially closed ring around the traversing opening 5. Bores 19 are embodied with similar diameters to those of the vias 13, 14 and likewise are provided with metallized inner walls. Bores 19 connect with one another the shielding plies 15, in each case, directly neighboring a toroidal coil 2, so that they act as vias for the two shielding plies 15.

Figure 2:
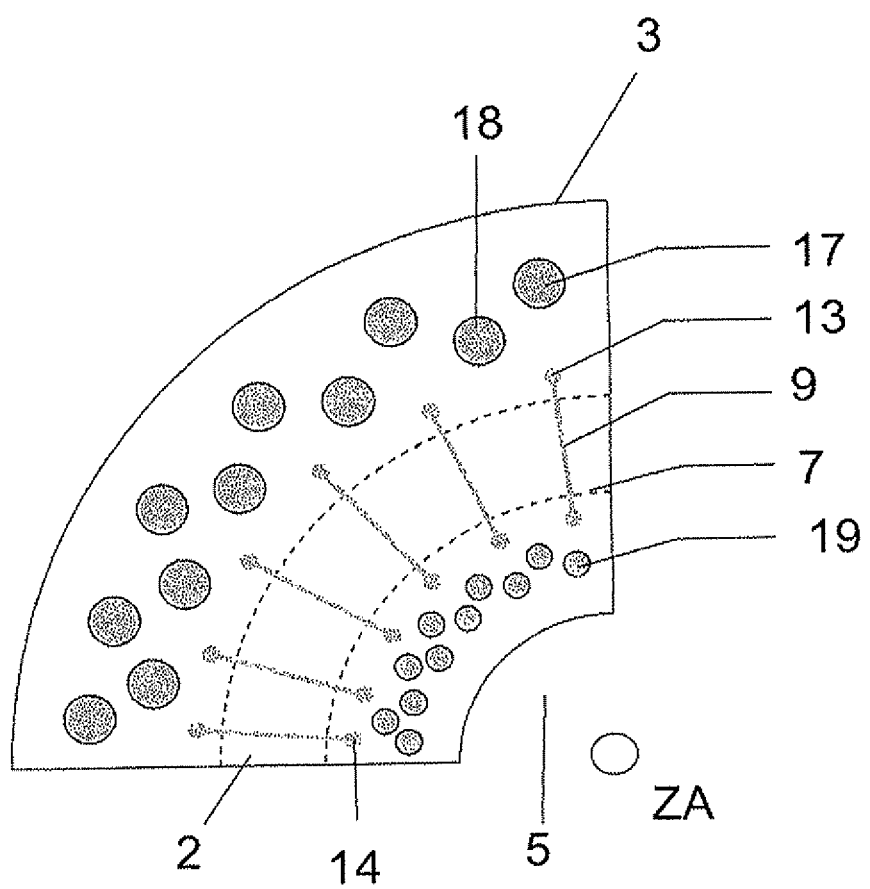
FIG. 2 is a plan view of a section of a circuit card plane of the conductivity sensor illustrated in FIG. 1.

Arranged along the outer periphery of the toroidal coils 2 formed by the outer vias 13 are further metallized bores 17, 18 extending parallel to the vias 13, 14. Bores 17 and 18 are arranged in two concentric rings around the toroidal coils 2, whose shared central axis is the rotational symmetry axis ZA of the toroidal coils 2. In such case, the bores 18 are arranged offset relative to the bores 17, as is shown in FIG. 2. In the sectional illustration shown in FIG. 1, the bores 18 would, consequently, actually not be shown. For purposes of better illustration, they are, however, indicated with dashed lines.

Bores 18 are conductively connected on their one end, in each case, with the outer shielding plies 15, which are arranged on the cover ply of the circuit card 3 or below the base ply of the circuit card 3, while they are insulated on their opposing end relative to the second shielding ply 15 by an insulating circuit card plane.

Bores 17 are conductively connected on their one end, in each case, with the shielding plies 15, which are arranged between the intermediate ply 21 and the planes, in which the conductor sections 11 are arranged, while they are insulated on their opposing end relative to the second shielding ply 15 by an insulating circuit card plane. Bores 17 and 18, thus, effect no electrical connection between the shielding plies 15, in contrast to situation with the bores 19.

While bores 17 and 18 do not act as vias between two circuit card planes, they are, nevertheless, otherwise embodied quite analogously to the vias 11, 14 or 19 and can be manufactured in the same way. In circuit card manufacture, such bores are known as so called blind hole vias.

Bores 17 and 18 extend, in such case, parallel to the vias 13 and 14 of the toroidal coil windings and extend perpendicularly in the stack direction through the same plies of the circuit card 3. In this way, there results an overlap of the shielding effected by the bores 17 with the shielding effected by the bores 18. This embodiment of the shielding along the outer periphery of the toroidal coils 2 is in its effect almost optimal, i.e. comparable with the shielding effect of the bores 19 traversing between the shielding plies 15, and avoids, at the same time, the forming of a short circuit path extending around the individual toroidal coils 2.

In the here illustrated example, the inner bores 19 are embodied as vies between the shielding plies 15, while the outer bores 17, 18 are conductively connected, in each case, with only one shielding ply 15. Alternatively, it would, however, also be possible, to connect the inner bores conductively, in each case, with only one shielding ply and to embody the outer bores as vias between the shielding plies.

FIG. 2 shows a plan view onto a section of the plane of the circuit card 3 located below the cutting plane A-A in FIG. 1. The section is a 90° sector of one of the two toroidal coils 2 and shows surrounding the toroidal coils 2 the internally metallized bores 17, 18, 19, which serve for the electrical shielding. Located in the illustrated circuit card plane are the first conductive traces 9, which, by way of the outer and inner vies 13 and 14, are connected with second conductive traces arranged in a second circuit card plane below that illustrated in FIG. 2. Beneath the illustrated circuit card plane is located, moreover, the toroidal core 7 of the toroidal coil 2 surrounded by the windings formed by the illustrated, and by the not shown, conductive traces and the vias 13, 14.

Between the traversing opening 5 and the inner periphery of the toroidal coil 2 formed by the inner vias 14 are located the internally metallized bores 19 for the electrical shielding, which conductively connect with one another a first shielding plane 15 arranged above the plane illustrated in FIG. 2 and a second shielding plane 15 arranged below the plane illustrated in FIG. 2 (compare FIG. 1). Bores 19 are provided in two concentric rings around the rotational symmetry axis ZA, wherein the bores are offset relative to one another at least by somewhat less than their radius, in order to produce an overlapping in the radial direction, so that the shielding effected by the bores 19 extends essentially gap free over the entire inner periphery of the toroidal coil 2. In the sectional illustration of FIG. 1, in each case, only one bore 19 of one of these rings is shown.

Along the outer periphery of the toroidal coil 2 formed by the outer vias 13 are arranged the metallized bores 17, 18. As already described based on FIG. 1, the bores 18 are conductively connected with a shielding ply 15 neighboring above the illustrated plane of the toroidal coil 2, while the bores 17 are connected with a shielding ply 15 neighboring below the illustrated plane of the toroidal coil 2. On their, in each case, other end, bores 17 and 18 are insulated from, in each case, the other shielding ply 15 by a not electrically conducting layer of the circuit card.

Bores 17 and 18 are arranged in concentric rings of different diameter around the rotational symmetry axis ZA. As in the case of the bores 19, bores 17 and 18 are arranged offset relative to one another at least by somewhat less than their radius, so that the shielding provided by the bores 17, 18 extends essentially gap free over the entire outer periphery of the toroidal coil 2.

As explained above, the exact shape of the rings, in which the bores 17, 18 and 19 are arranged, is not decisive. The rings can be e.g. circular, elliptical, polygonal or an irregular shape, so long as the bores 17, 18, 19, in each case, lie on an essentially closed path.

Besides the examples of embodiments illustrated in FIGS. 1 and 2, other examples of embodiments of the invention can be advantageous in given cases. For example, the two toroidal coils of the conductivity sensor can be arranged, instead of coaxially axially one after the other, also coaxially coplanarly with a shared central axis, or coplanarly next to one another with parallel central axes. In the case of coplanarly arranged coils, only two traversing electrical shielding plies are required, which, as regards the stack direction of the circuit card planes, are arranged above and below the planes, in which the toroidal coil windings and, in given cases, the toroidal coil cores are located. The arrangement of the bores for shielding the toroidal coils along their inner, or outer, peripheries is in these examples of embodiments analogous to those of the example illustrated in FIGS. 1 and 2.

The invention claimed is:

1. A conductivity sensor for measuring conductivity of a medium surrounding the conductivity sensor, comprising:
   a first toroidal coil, which surrounds a first traversing opening for accommodating the medium and which serves for inducing an electrical current in the medium; and
   a second toroidal coil, which surrounds a second traversing opening for accommodating the medium and for registering a magnetic field produced by the induced electrical current, wherein:
   at least one of said toroidal coils has a plurality of first conductor sections, which extend in a first plane of a multi-ply circuit card, a plurality of second conductor sections, which extend in a second plane of said circuit card, and a plurality of vias, which connect said first conductor sections with said second conductor sections;
   said first conductor sections, said second conductor sections and said vias together form the windings of said first toroidal coil;
   said at least one toroidal coil is surrounded by a plurality of internally metallized bores, which are arranged in such a manner, that they act as electrical shielding of said toroidal coil;
   said internally metallized bores extend essentially parallel to said vias, especially wherein said bores and said vias extend essentially perpendicular to the plies of said circuit card;
   said plurality of internally metallized bores comprise internally metallized bores of a first type, which are arranged along an essentially closed ring surrounded by said at least one toroidal coil and extend around said traversing opening surrounded by said toroidal coil;
   in at least one additional third plane of the circuit card, an electrical shielding ply, especially of an electrically conductive material, especially copper, is arranged;
   said at least one toroidal coil is arranged in the stack direction of said circuit card before or behind said shielding ply;
   in the third plane of said circuit card, a first electrical shielding ply is arranged and, in an additional, fourth plane of said circuit card, a second electrical shielding ply is arranged;
   said at least one toroidal coil with reference to the stack direction of said circuit card is arranged between said first and second shielding plies;
   each of said internally metallized bores of said first type is directly connected with only one of said electrical shielding plies; and
   said internally metallized bores of second type connect said first and second electrical shielding plies with one another.

2. The conductivity sensor as claimed in claim 1, wherein:
   at least one of said toroidal coils has a toroidal core, especially one composed of at least one annular foil or a solid or layered core material.

3. The conductivity sensor as claimed in claim 1, wherein:
   said first and second toroidal coils are arranged coplanarly and coaxially; and
   said first and second toroidal coils have a shared central axis, especially a rotational symmetry axis.

4. The conductivity sensor as claimed in claim 1, wherein:
   said first and second toroidal coils are arranged coplanarly, axially parallelly and adjoin one another; and
   said first and second toroidal coils have central axes, especially rotational symmetry axes, which are spaced from one another.

5. The conductivity sensor as claimed in claim 1, wherein:
   said first and second toroidal coils are arranged coaxially and axially sequenced one after the other and have a shared central axis, especially a rotational symmetry axis; and
   at least one shielding ply for magnetic shielding is arranged in said circuit card between said toroidal coils.

6. The conductivity sensor as claimed in claim 5, wherein:
   said at least one shielding ply for magnetic shielding comprises a high permeability material, especially one with a relative permeability of more than 1000.

7. A conductivity sensor for measuring conductivity of a medium surrounding the conductivity sensor, comprising:
   a first toroidal coil, which surrounds a first traversing opening for accommodating the medium and which serves for inducing an electrical current in the medium; and
   a second toroidal coil, which surrounds a second traversing opening for accommodating the medium and for registering a magnetic field produced by the induced electrical current, wherein:
   at least one of said toroidal coils, which surrounds a second traversing opening for accommodating the medium and for registering a magnetic field produced by the induce electrical current, wherein:

at least one of said toroidal coils has a plurality of first conductor sections, which extend in a first plane of a multi-ply circuit card, a plurality of second conductor sections, which extend in a second plane of said circuit card, and a plurality of vias, which connect said first conductor sections with said second conductor sections;

said first conductor sections, said second conductor sections and said vias together form the windings of said first toroidal coil;

said at least one toroidal coil is surrounded by a plurality of internally metallized bores, which are arranged in such a manner, that they act as electrical shielding of said toroidal coil;

said internally metallized bores extend essentially parallel to said vias, especially wherein said bores and said vias extend essentially perpendicular to the plies of said circuit card;

said plurality of internally metallized bores comprise internally metallized bores of a first type, which are arranged along an essentially closed ring surrounded by said at least one toroidal coil and extend around said traversing opening surrounded by said toroidal coil;

in at least one additional third plane of the circuit card, an electric shielding ply, especially of an electrically conductive material, especially cooper, is arranged;

said at least one toroidal coil is arranged in the stack direction of said circuit card before or behind said shielding ply;

in the third plane of said circuit card, a first electrical shielding ply is arranged and, in an additional, fourth plane of said circuit card, a second electrical shielding ply is arranged;

said at least one toroidal coil with reference to the stack direction of said circuit card is arranged between said first and second shielding plies;

said internally metallized bores of the first type connect said first and second electrical shielding plies with one another; and each of said internally metallized bores of the second type is directly connected with only one of said electrical shielding plies.

8. The conductivity sensor as claimed in claim 7, wherein:

said internally metallized bores of second type comprise a first group of bores, which are directly connected with said first electrical shielding ply, and a second group of bores, which are conductively connected with said second electrical shielding ply; and said first and second electrical shielding plies are arranged on opposing sides of said at least one toroidal coil.

9. The conductivity sensor as claimed in claim 8, wherein:

said bores of said first and second groups extend in the stack direction of said circuit card over the same circuit card plies as said vias of said at least one toroidal coil.

* * * * *